United States Patent [19]

Yu

[11] Patent Number: 6,110,181
[45] Date of Patent: Aug. 29, 2000

[54] THREAD CARRIER PLATE DEVICE AND METHOD

[75] Inventor: Ken-Jen Yu, Tazpei, Taiwan

[73] Assignee: Veterans General Hospital-Taipei, VACRS, Taipei, Taiwan

[21] Appl. No.: 09/248,199

[22] Filed: Feb. 10, 1999

[51] Int. Cl.[7] .................................................. A61B 17/04

[52] U.S. Cl. ............................... 606/119; 600/1; 606/148; 606/139

[58] Field of Search ............................... 606/139, 1, 148, 606/119; 600/206, 207, 210, 211, 37; 128/898

[56] References Cited

U.S. PATENT DOCUMENTS

| | | | |
|---|---|---|---|
| 5,209,754 | 5/1993 | Ahluwalia | 606/119 |
| 5,643,285 | 7/1997 | Rowden et al. | 606/119 |
| 5,743,853 | 4/1998 | Lauderdale | 600/210 |
| 5,746,742 | 5/1998 | Runciman et al. | 606/69 |

*Primary Examiner*—Gary Jackson
*Attorney, Agent, or Firm*—Robert L. Shaver; Frank J. Dykas

[57] ABSTRACT

A device and method for helping surgeons pass the sutures through the vagina into the abdominal cavity during an operation of laparoscopic assisted vaginal hysterectomy (LAVH). The device utilizes two long plates having a pair of small holes on both ends. The plates are used to pass the thread into the abdominal cavity through the opening of the colpotomy at fornices of the vagina.

13 Claims, 14 Drawing Sheets

THREAD CARRIER PLATE DEVICE AND METHOD

BACKGROUND OF THE INVENTION

1. Field of the Invention

The present invention assists the surgeon in a laparoscopic assisted vaginal hysterectomy (LAVH). The thread carrier device makes it easier to suture through the vagina into the abdominal cavity during the operation. This tool improves the accessibility and safety factors of the operation.

2. Description of the Prior Art

All over the world, LAVH is a very common procedure applied in gynecologic laparoscopic surgery. However, a large uterus is not easy to be pulled down into the vagina to divide the uterine cardinal ligaments during the LAVH operation. A hypertrophied cervix narrows the limited space of the vagina, and also increases the level of difficulty in the operation. Additional objects, advantages and novel features of the invention will be set forth in part in the description as follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

The main goal of the present invention, "Thread Carrier Plate Device and Method", is to make an assisted approach to secure ligation and cutting of the uterine cardinal ligaments in the procedure of LAVH. The implementation of the present invention, "Thread Carrier Plate Device and Method", is to use a long plate to carry the thread which leads the thread from the vagina into the cardinal ligaments on both sides of uterus. This is done so that the uterine cardinal ligaments can be tied securely.

Since the plates are quite flexible, it will firmly hold onto the surrounding tissue of the opening at the vaginal fornices, and will also prevent air leakage from the abdominal cavity during the operation. This will allow for a safer and more convenient process to complete the operation.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

BRIEF DESCRIPTION OF THE INVENTION

To further comprehend the present invention, the inventor describes the present invention in detail with one preferred embodiment and attached figures as follows.

DESCRIPTION OF FIGURES

NUMBERS IN FIGURES

1 . . . Thread delivery plate,

2 . . . Thread traction plate,

3 . . . Anterior of Plate,

4 . . . Posterior of Plate.

11 . . . Small holes

12 . . . Left wing of plate

13 . . . Head of thread delivery plate

14 . . . Tail end of thread delivery plate

15 . . . Sutures

21 . . . Right wind of plate

22 . . . Mushroom shaped protrusion of thread traction plate

DESCRIPTION OF THE PREFERRED EMBODIMENTS

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

While there is shown and described the present preferred embodiment of the invention, it is to be distinctly understood that this invention is not limited thereto but may be variously embodied to practice within the scope of the following claims.

Figure 1:
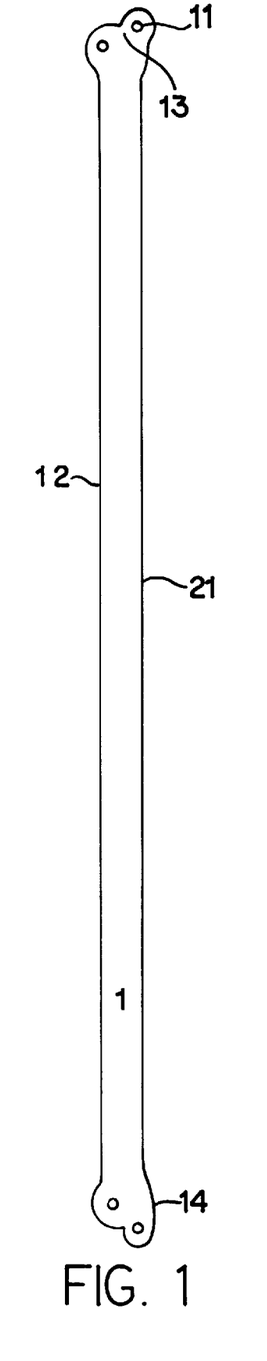
FIG. 1. Frontal view of thread delivery plate.
Figure 2:
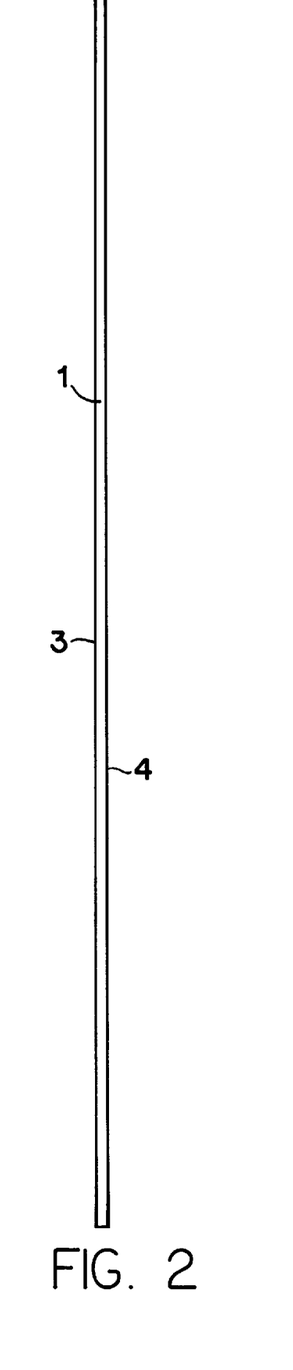
FIG. 2. Lateral view of thread delivery plate.
Figure 3:
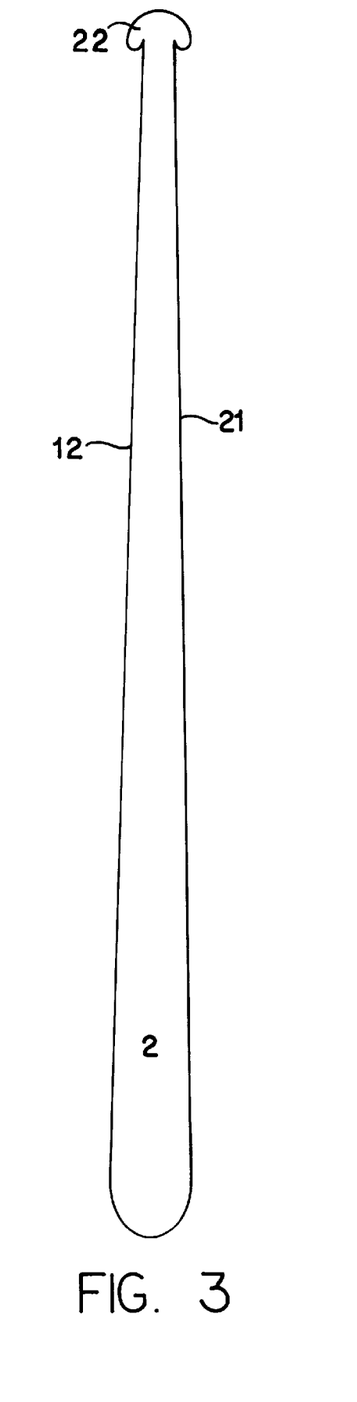
FIG. 3. Frontal view of thread traction plate.
Figure 4:
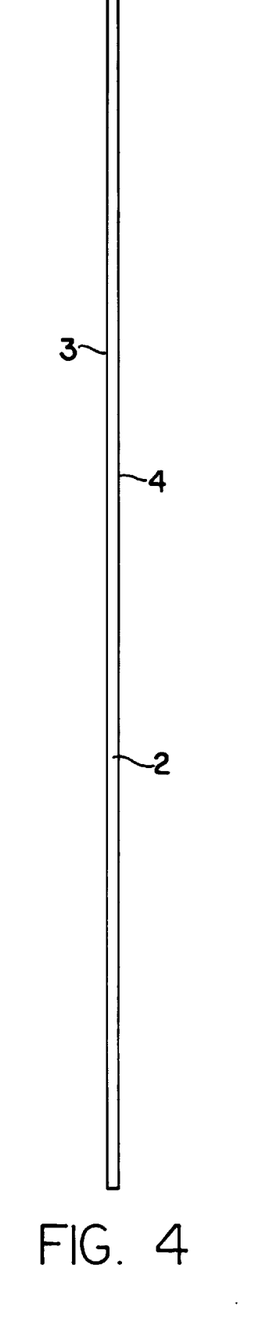
FIG. 4. Lateral view of thread traction plate.
Figure 5:
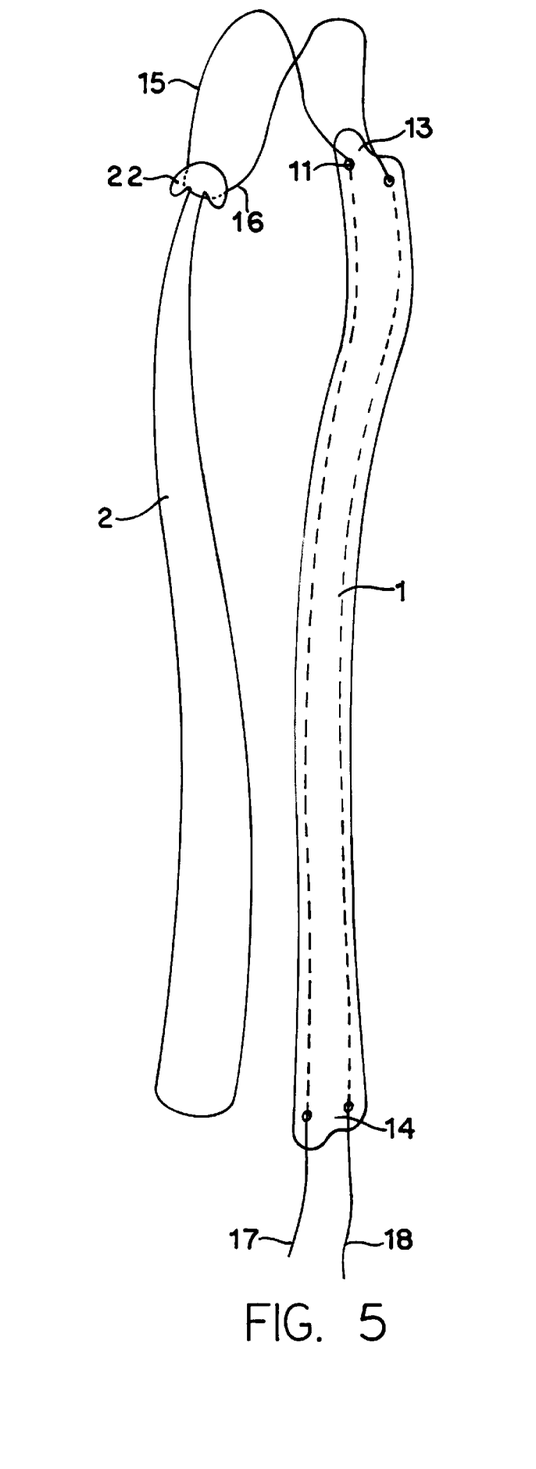
FIG. 5. An embodiment of the present invention; A thread has been placed properly on the thread delivery plate and the thread loop was hooked in the mushroom shaped head of a thread traction plate.

The present invention, "Thread Carrier Plate Device and Method", is formed of two long plastic plates. FIG. 1 is the frontal view of the present invention. The present invention can be divided into the following parts: two long plastic plates—the thread delivery plate (1) and the thread traction plate (2). The other parts on the plate are a left wing (12), a thread delivery head (13), a tail (14), a right wing (21), a mushroom shaped protrusion (22). Each thread delivery head (13) and tail (14) of the thread delivery plate (1) have two small holes (11). The thread traction plate (2) has a mushroom-shaped protrusion which helps the surgeon to hook the thread loop.

The device is used with a suture thread (15) having a first end (17), a second end (18) and a central portion or loop (16). The thread delivery plate (1), either of the thread delivery head (13) or tail (14) of the present invention, have different shapes, colors, and designs to help the user recognize the left and right wings of the plate. These different shapes, colors and designs can be generally referred to as "distinguishing means". In a typical design, the right wing (21) is longer or has a larger curvature than the left wing (12). This is so that the surgeon can easily tell the left or right side of the thread delivery plate to prevent causing a misturned plate. Also, the small holes (11) on the thread delivery head (13) or the tail (14) are good for holding and adjusting the length of sutures (15). The mushroom shaped protrusion (22) of the traction plate (2) can conveniently hook and hold the suture loop.

The materials for this device must have sufficient flexibility to bend properly with the local structure of the genital tract. It is vital that the device can fit firmly between the surrounding tissues and prevent air leakage from the abdominal cavity during the operation. The materials could be made of plastic, metal, or fibrous textiles for examples. Some parts of this device including, the thread delivery head (13), the small holes (11), the mushroom shaped protrusion (22) and the tail (14), may be compounded arbitrarily. The color of the left wing (12) is different from the right wing (21) so that the surgeon can distinguish a flipped plate more easily. All plates are light in weight, economical, and easy to use.

Figure 6:
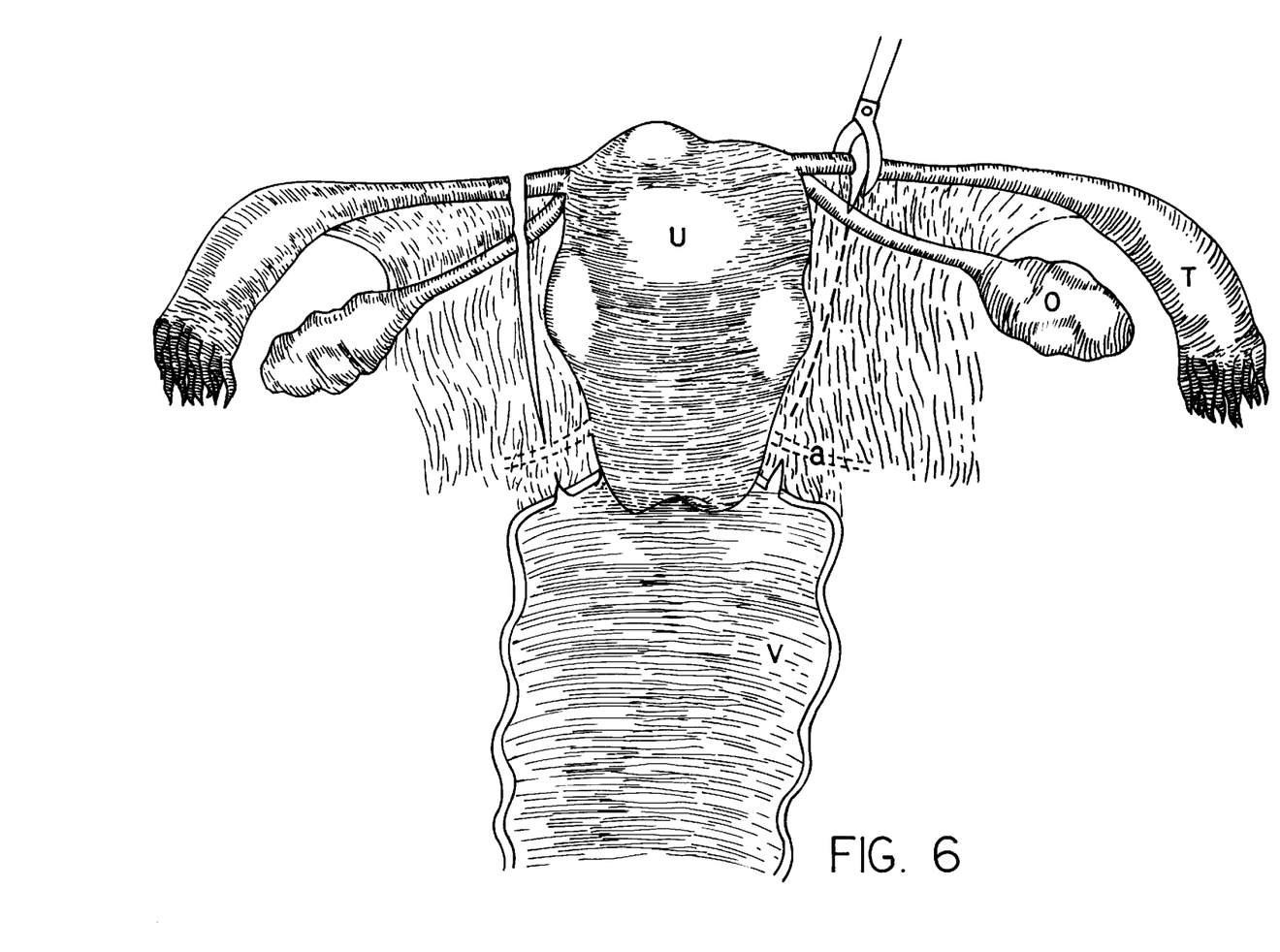
FIG. 6. Direct view of the embodiment of the present invention in operation of LAVH.

The inventor describes the present invention in detail with one preferred embodiment and attached figures as follows:

Referring to FIG. 6, Laparoscopically, the surgeon uses a laparoscopic scissors to cut the round ligaments, oviduct (T), and the broad ligament of uterus (U). The surgeon cuts downward until it's near the uterine artery (a). From the vagina, we make first and second colpotomies on the anterior and the posterior of the vaginal fornices. Then the uterine cardinal ligaments are cut upward from the vagina until it is difficult to do so.

Figure 7:
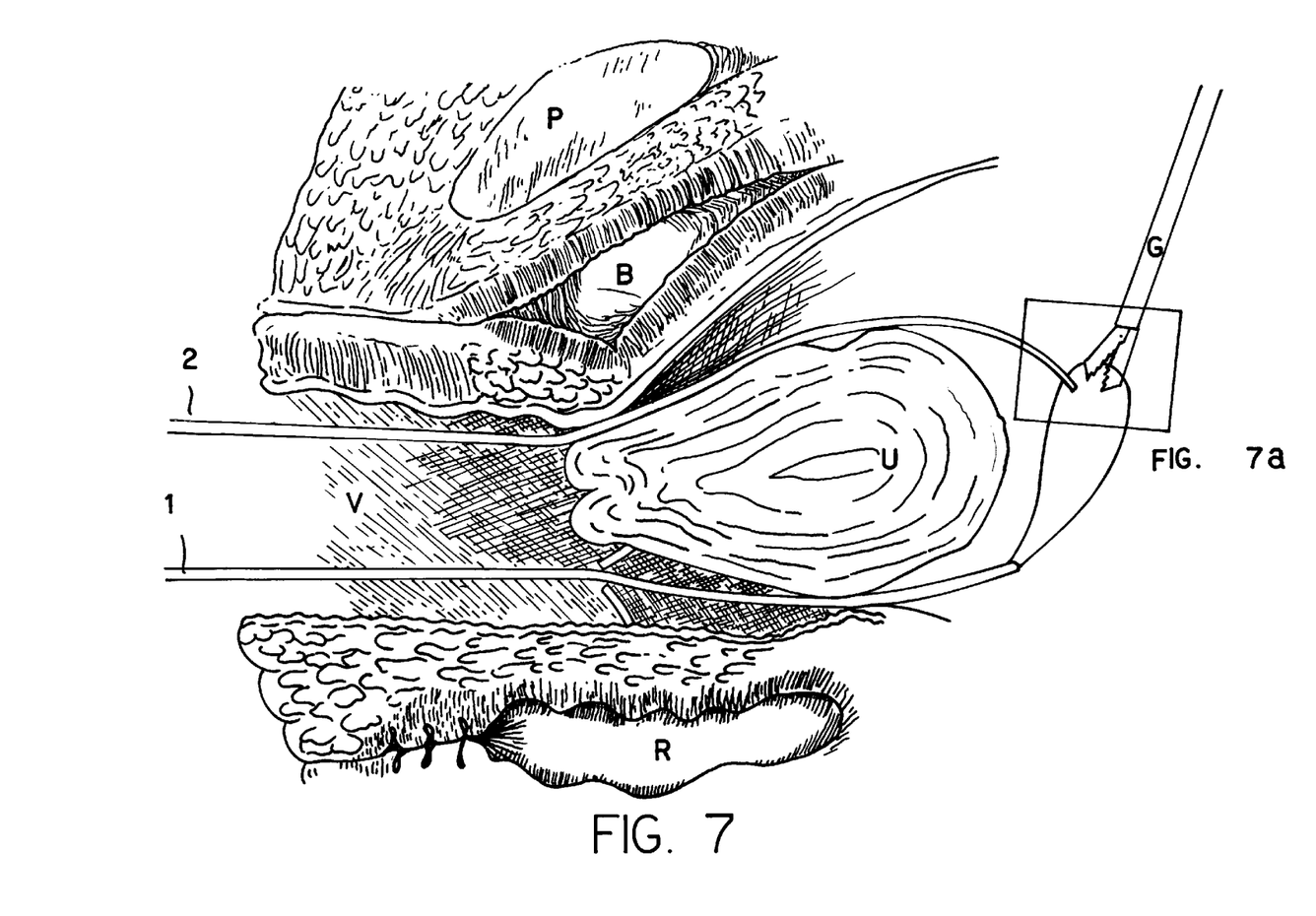
FIG. 7. Lateral view of the embodiment of the present invention in operation of LAVH; The thread delivery plate inserted into the abdominal cavity through the posterior colpotomy and the thread traction plate in the anterior colpotomy.
Figure 7A:
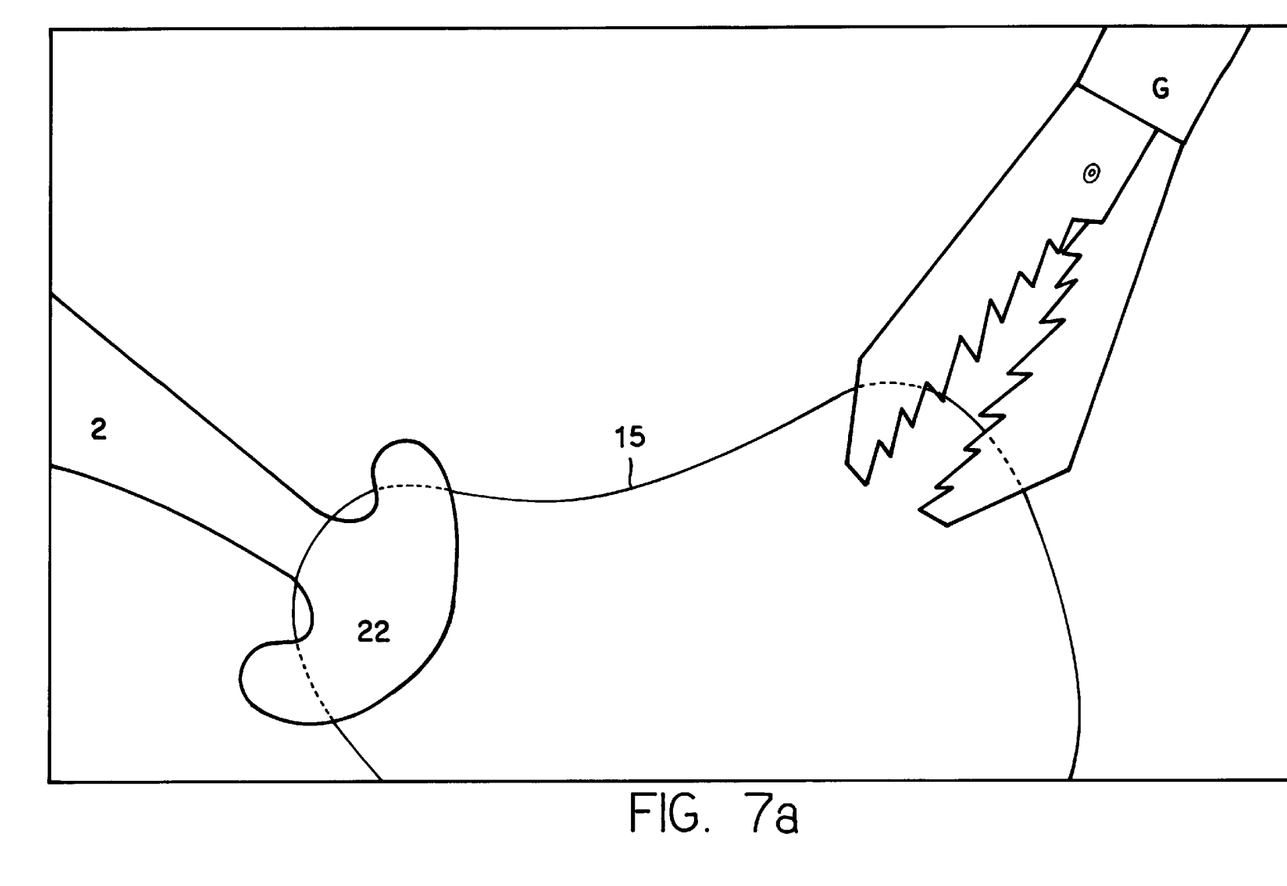
FIG. 7A. The insertion illustration in FIG. 7 is shown; The thread loop on the head of a thread delivery plate had been grasped and hooked onto the mushroom shaped protrusion of a thread traction plate.
Figure 8:
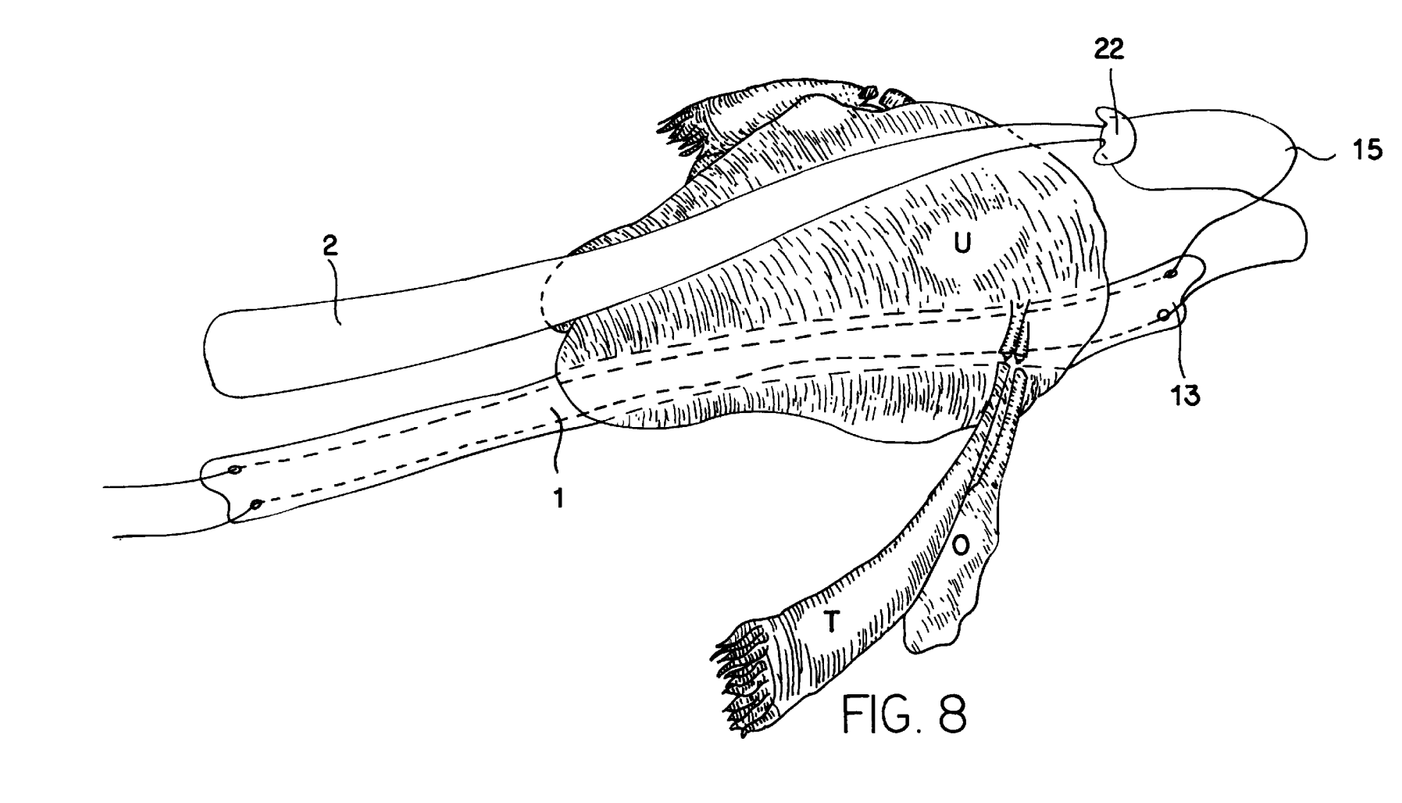
FIG. 8. An oblique view of the embodiment in an operation of LAVH; Thread delivery plate carried with a thread was inserted posterior to the uterus. The thread traction plate was placed anterior to the uterus. The thread loop was hooked onto the mushroom shaped head of a thread traction plate.
Figure 9:
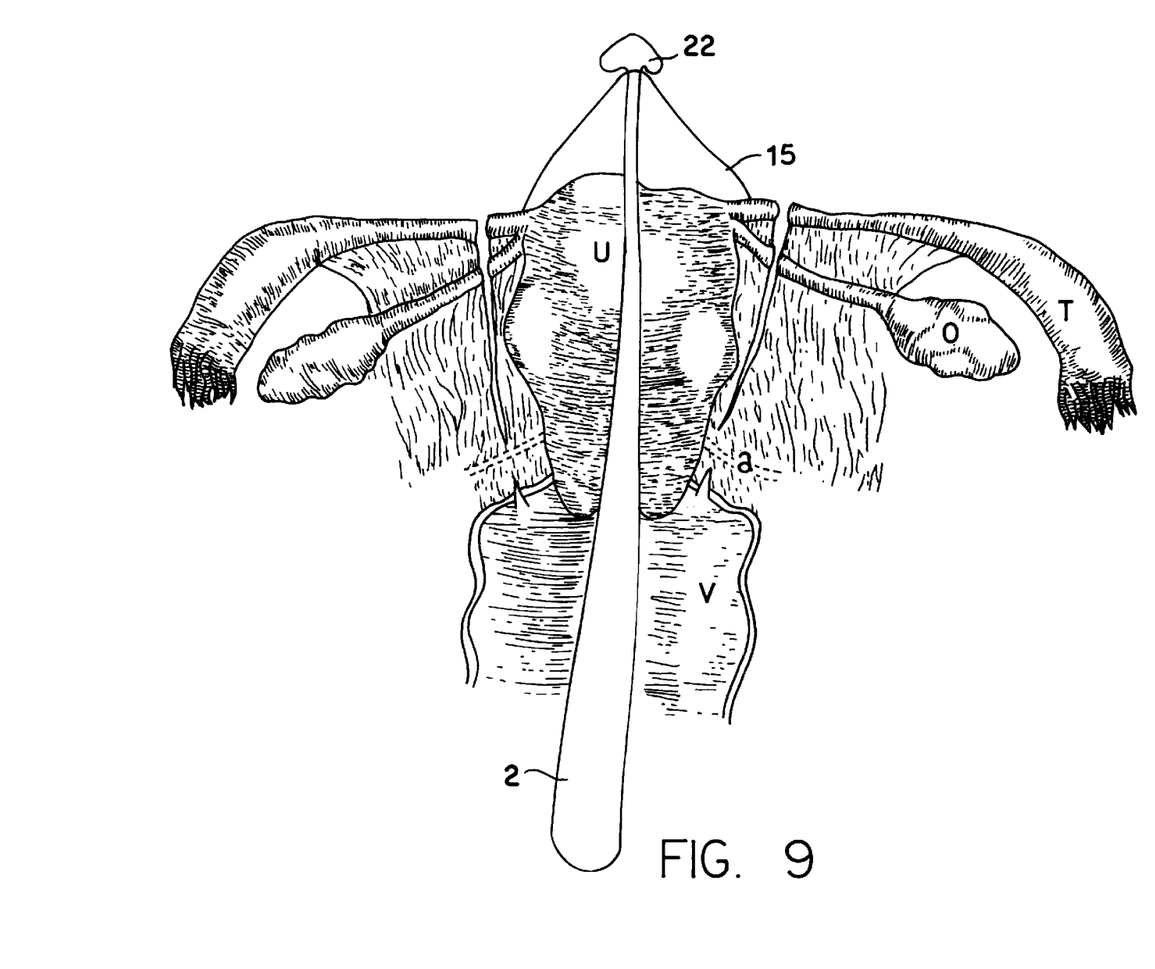
FIG. 9. Direct view of the embodiment of the present invention in operation of LAVH; The thread loop had been hooked onto the mushroom shaped protrusion and the thread loop was placed on the both sides of the uterus.
Figure 10:
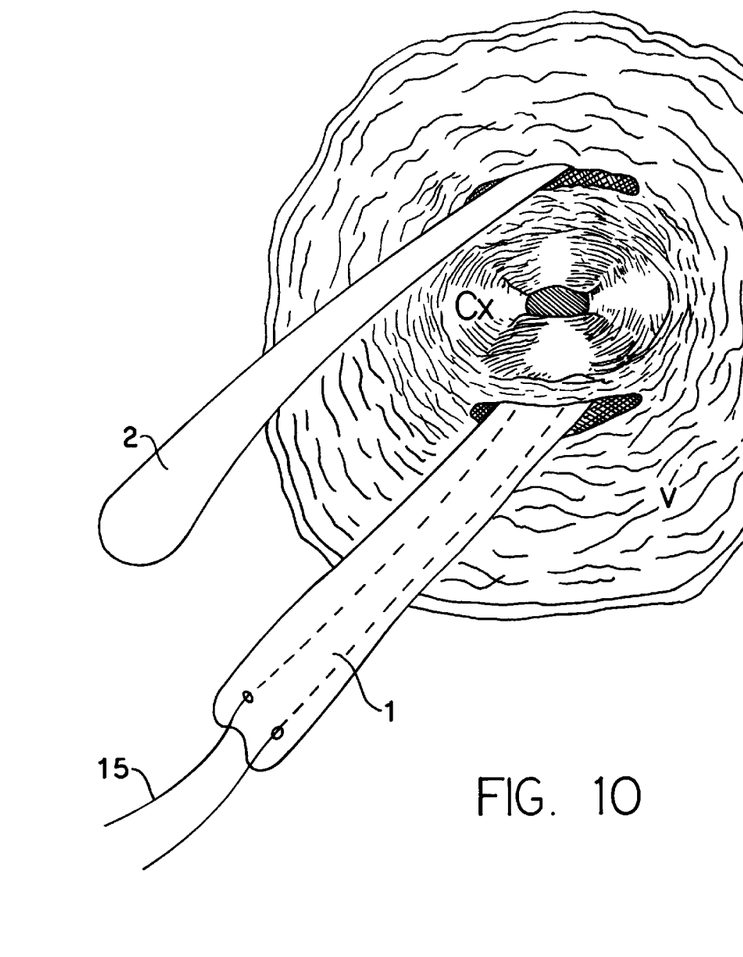
FIG. 10. A vaginal view of the embodiment of the present invention in operation of LAVH; The thread delivery plate with a thread and the thread traction plate were inserted into the abdominal cavity through the anterior and the posterior colpotomies respectively.
Figure 11:
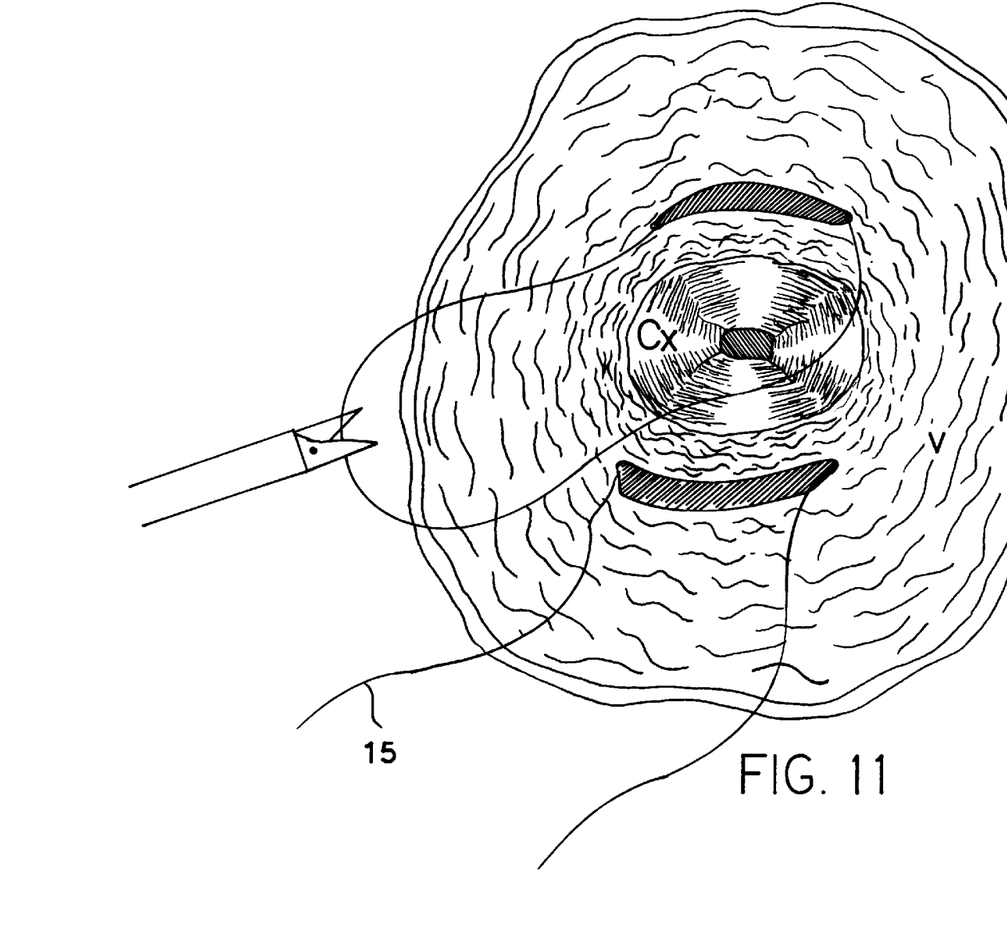
FIG. 11. A vaginal view of the present invention after removal of plates and cutting the thread loop; The thread loop was brought out of the abdominal cavity by the thread traction plate through the anterior colpotomy. The thread delivery plate had been removed. The thread loop is going to be cut into 2 sutures.
Figure 12:
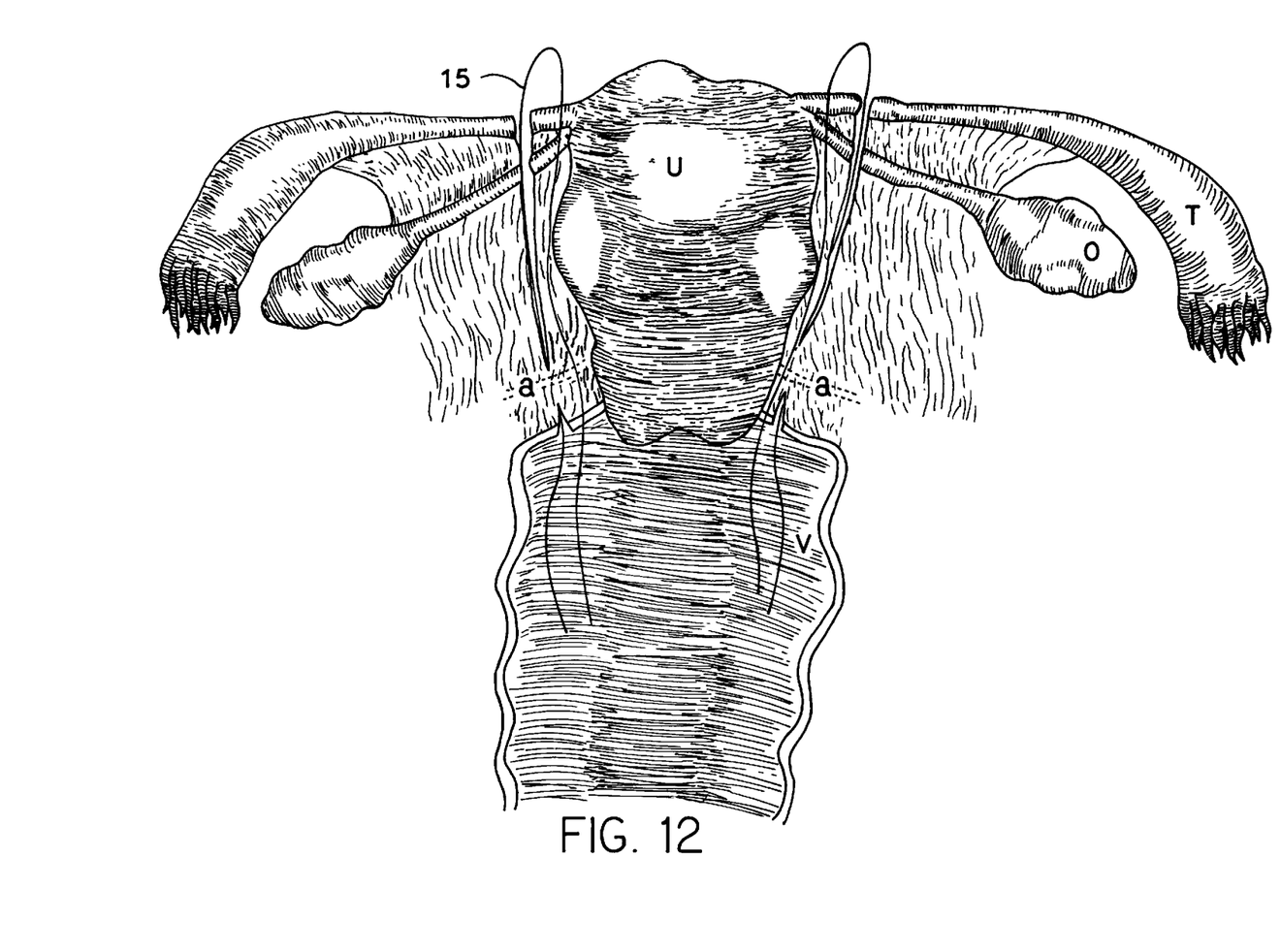
FIG. 12. Direct view after the embodiment of the present invention has been removed; The thread loops on both ardinal ligaments.
Figure 13:
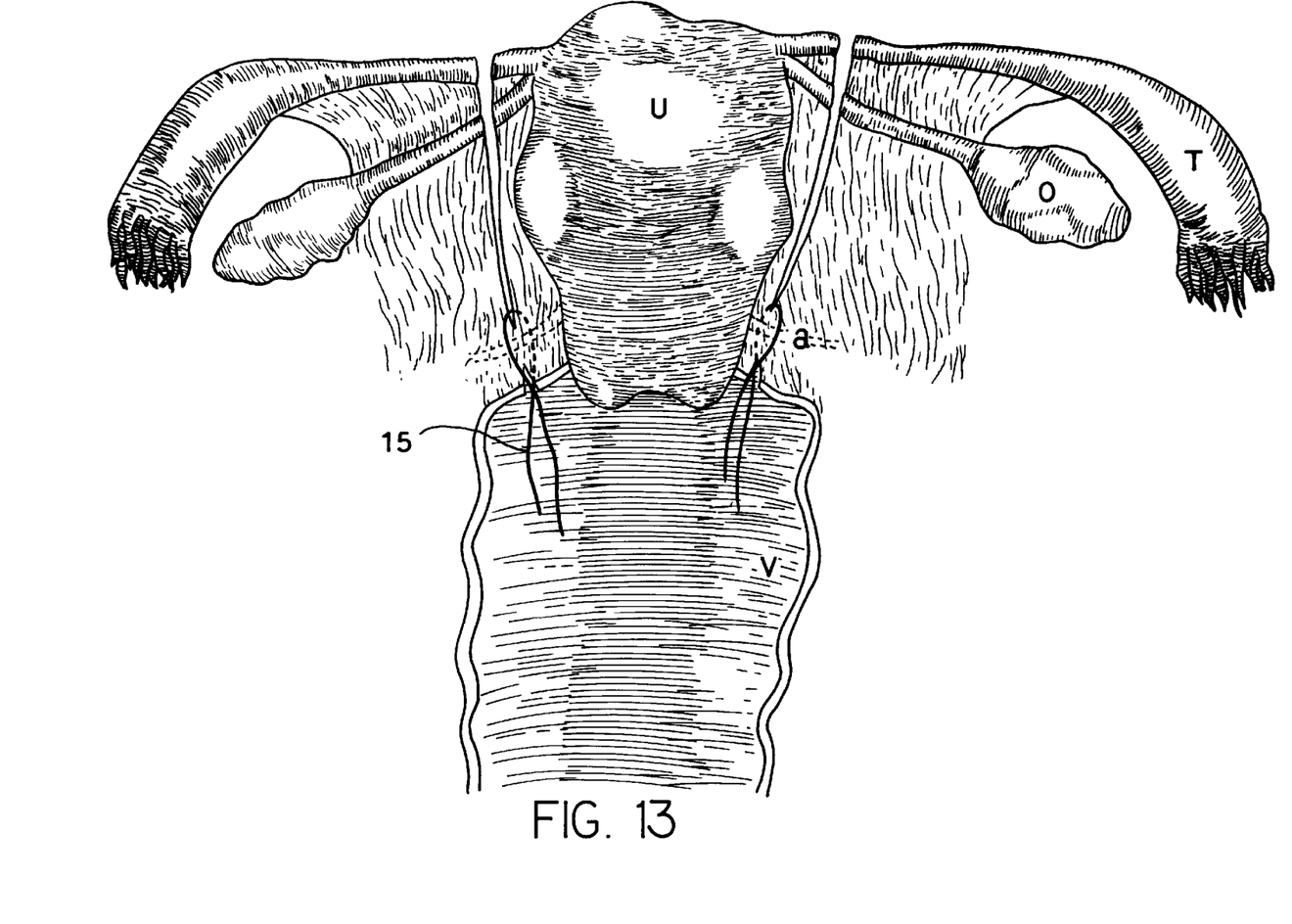
FIG. 13. Direct view after the embodiment of the present invention is removed; The thread loops on both cardinal ligaments had been tied securely.

Referring to FIGS. 7, 8, and 9, the surgeon inserts the thread delivery plate (1) with sutures into the abdominal cavity through the first opening of the colpotomy. Then the traction plate (2) stretches into the other opening of colpotomy. The cervix is held by a grasper and keeps downward traction, so that the uterus is pulled tightly against the vagina to prevent air leakage from the abdominal cavity. Then the suture loop on the threading delivery plate (1) is grasped and pulled to make a big loop. The notch shape of the thread delivery plate helps make the grasping process easier. Then the big loop is placed around the uterus and into the cut cardinal ligaments. The suture loop is then hooked by the mushroom-shaped protrusion (22) of the traction plate (2). Then the thread traction plate is pulled with the suture loop out of the vagina (FIGS. 10, 11). After cutting the loop, both sides (FIG. 12) of the uterine cardinal ligaments are ligatured individually (FIG. 13). After the uterine cardinal ligaments are cut along the uterus sides, the uterus is taken out and the vaginal cuff is sewn to complete the operation.

There are two small holes (11) on each end, of the thread delivery plate. Either end can be used as the thread delivery head into the abdominal cavity to achieve a convenient and practical application. It sturdily holds the sutures and makes it easier to adjust the loop size during the operation. The small holes on the two ends (11) can prevent the sutures from entangling together or tying knots. Color or shape of the left wing (12) and right wing (21) are different so that the surgeon can be assured that the long plate is not misturned, thus preventing the sutures from entangling together, or tying knots.

For those patients with an enlarged uterus or hypertropic cervix, the "Thread Carrier Plate Device and Method" facilitates rapid and secure ligations of the uterine cardinal ligament during the procedure of laparoscopic assisted vaginal hysterectomy (LAVH).

Another preferred embodiment of the invention is a method of performing laparoscopic assisted vaginal hysterectomy, as described above.

From the foregoing description, it will be apparent that various changes may be made without departing from the spirit and scope of the invention as defined by the following claims.

I claim:

1. A thread carrier plate device for use with a suture thread having a first end, a second end and a central portion, said thread carrier plate device comprising:

an elongated thread delivery plate for insertion of a suture into the abdominal cavity through the opening of a first colpotomy, said elongated thread delivery plate having a delivery head for insertion into the first colpotomy and a delivery tail for grasping by a user, wherein said delivery head has a pair of thread receiving holes therethrough for receiving said thread central portion, wherein said delivery tail has a pair of thread receiving hole therethrough for receiving said thread ends; and an elongated thread traction plate for insertion of a suture into the abdominal cavity through the opening of a second colpotomy, said elongated thread traction plate having a traction head formed to grasp said central portion length of said thread.

2. The thread carrier plate device of claim 1 wherein said traction head is a mushroom shaped protrusion.

3. The thread carrier plate device of claim 1 wherein said elongated thread delivery plate and said elongated thread traction plate are comprised of plastic.

4. The thread carrier plate device of claim 1 wherein said elongated thread delivery plate and said elongated thread traction plate are comprised of metal.

5. The thread carrier plate device of claim 1 wherein said elongated thread delivery plate and said elongated thread traction plate are comprised of fibrous textile material.

6. The thread carrier plate device of claim 1 wherein said elongated thread delivery plate further comprises a left wing and a right wing, wherein said thread delivery plate further comprises distinguishing means for allowing said user to distinguish said left wing from said right wing.

7. The thread carrier plate device of claim 6 wherein said distinguishing means is the shape of the thread delivery head.

8. The thread carrier plate device of claim 6 wherein said distinguishing means is the shape of the thread delivery tail.

9. The thread carrier plate device of claim 6 wherein said right wing is longer than said left wing.

10. The thread carrier plate device of claim 6 wherein said right wing is colored differently than said left wing.

11. The thread carrier plate device of claim 1 wherein said elongated thread traction plate further comprises a left wing and a right wing, wherein said thread traction plate further comprises distinguishing means for allowing said user to distinguish said left wing from said right wing.

12. The thread carrier plate device of claim 1 wherein said elongated thread delivery plate further comprises deep notches at both ends for allowing a user to more easily grasp said thread central portion length from said thread delivery head.

13. A thread carrier plate device for use with a suture thread having a first end, a second end and a central portion, said thread carrier plate device comprising:

an elongated thread delivery plate for insertion of a suture into the abdominal cavity through the opening of a first colpotomy, said elongated thread delivery plate having a delivery head for insertion into the first colpotomy and a delivery tail for grasping by a user, wherein said delivery head has a pair of thread receiving holes therethrough for receiving said thread central portion, wherein said delivery tail has at a pair of thread receiving holes therethrough for receiving said thread ends, wherein said elongated thread delivery plate further comprises a left wing and a right wing, wherein said thread delivery plate further comprises distinguishing means for allowing said user to distinguish said left wing from said right wing, wherein said elongated thread delivery plate further comprises deep notches at both ends for allowing a user to more easily grasp said thread central portion length from said thread delivery head; and an elongated thread traction plate for insertion of a suture into the abdominal cavity through the opening of a second colpotomy, said elongated thread traction plate having a mushroom shaped traction head formed to grasp said central portion length of said thread.

\* \* \* \* \*